(12) United States Patent
Ganssle et al.

(10) Patent No.: US 10,422,914 B2
(45) Date of Patent: Sep. 24, 2019

(54) MAGNETIC RESONANCE SYSTEMS AND METHODS EMPLOYING MULTI-SHAPE PULSE SEQUENCES FOR PARALLEL MEASUREMENTS

(71) Applicant: HALLIBURTON ENERGY SERVICES, INC., Houston, TX (US)

(72) Inventors: Paul Joseph Ganssle, Houston, TX (US); Shriram Sarvotham, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 424 days.

(21) Appl. No.: 15/313,508

(22) PCT Filed: Jun. 9, 2014

(86) PCT No.: PCT/US2014/041503
§ 371 (c)(1),
(2) Date: Nov. 22, 2016

(87) PCT Pub. No.: WO2015/191025
PCT Pub. Date: Dec. 17, 2015

(65) Prior Publication Data
US 2017/0153352 A1  Jun. 1, 2017

(51) Int. Cl.
*G01V 3/32* (2006.01)
*G01N 15/08* (2006.01)
(Continued)

(52) U.S. Cl.
CPC .............. *G01V 3/32* (2013.01); *E21B 47/00* (2013.01); *G01N 15/088* (2013.01);
(Continued)

(58) Field of Classification Search
CPC ...... G01N 15/088; G01N 24/081; G01V 3/32; E21B 47/00; G01R 33/44; G01R 33/50
See application file for complete search history.

(56) References Cited

U.S. PATENT DOCUMENTS 5,212,447 A * 5/1993 Paltiel ............. G01R 33/56341
324/300
6,541,969 B2 * 4/2003 Sigal .................... G01N 24/081
324/303
(Continued)

FOREIGN PATENT DOCUMENTS

| WO | 92/09901 | 6/1992 |
|---|---|---|
| WO | 2002/086541 | 10/2002 |
| WO | 2015/191025 | 12/2015 |

OTHER PUBLICATIONS

EP Application Serial No. 14894663.5, Supplemental European Search Report; dated Dec. 8, 2017, 8 pages.
(Continued)

*Primary Examiner* — Patrick Assouad
*Assistant Examiner* — Haidong Zhang
(74) *Attorney, Agent, or Firm* — Gilliam IP PLLC

(57) ABSTRACT

A magnetic resonance method includes providing a pulse sequence that affects different measurement regions in presence of a magnetic field gradient, the pulse sequence having multiple pulse shapes and multiple characteristic interecho intervals (TEs). The method also includes storing echo information resulting from the pulse sequence

17 Claims, 4 Drawing Sheets

(51) Int. Cl.
*G01R 33/50* (2006.01)
*E21B 47/00* (2012.01)
*G01N 24/08* (2006.01)
*G01R 33/44* (2006.01)

(52) U.S. Cl.
CPC .......... *G01N 24/081* (2013.01); *G01R 33/44* (2013.01); *G01R 33/50* (2013.01)

(56) References Cited

U.S. PATENT DOCUMENTS

| | | |
|---|---|---|
| 6,566,874 B1 * | 5/2003 | Speier .................. G01N 24/081 324/303 |
| 6,597,170 B1 | 7/2003 | Beard et al. |
| 6,646,438 B2 * | 11/2003 | Kruspe .................. G01R 33/50 324/303 |
| 6,859,034 B2 | 2/2005 | Chen |
| 7,852,077 B2 | 12/2010 | Song et al. |
| 2002/0033699 A1 | 3/2002 | Toufaily et al. |
| 2003/0071620 A1 | 4/2003 | Reiderman |
| 2013/0093422 A1 | 4/2013 | Morys et al. |
| 2013/0234704 A1 | 9/2013 | Huerlimann et al. |

OTHER PUBLICATIONS

PCT International Search Report and Written Opinion, dated Mar. 26, 2015, Appl No. PCT/US2014/041503, "Magnetic Resonance Systems and Methods Employing Multi-Shape Pulse Sequences for Parallel Measurements," Filed Jun. 9, 2014, 16 pgs.

* cited by examiner

FIG. 1
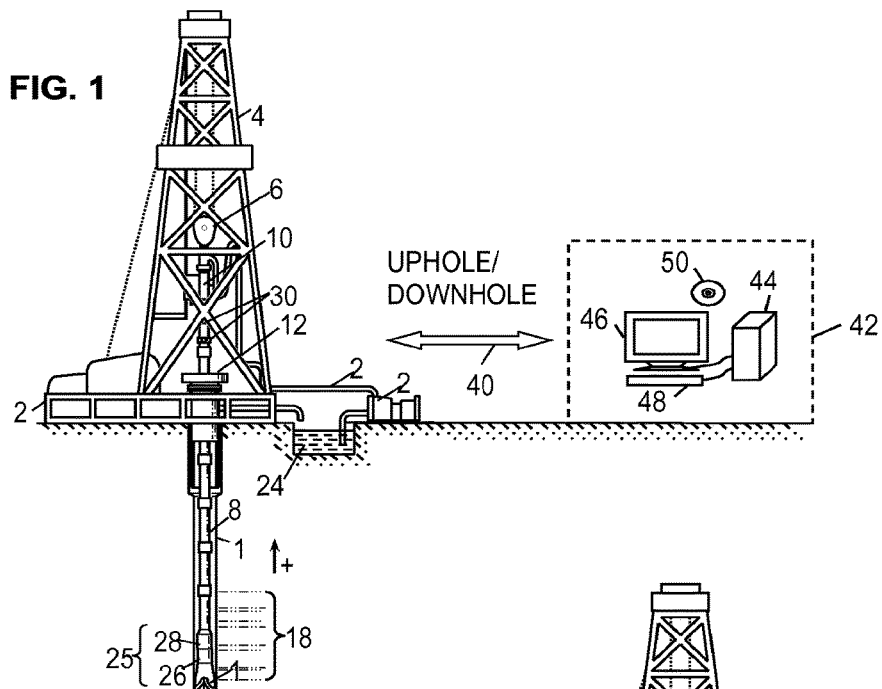
FIG. 2
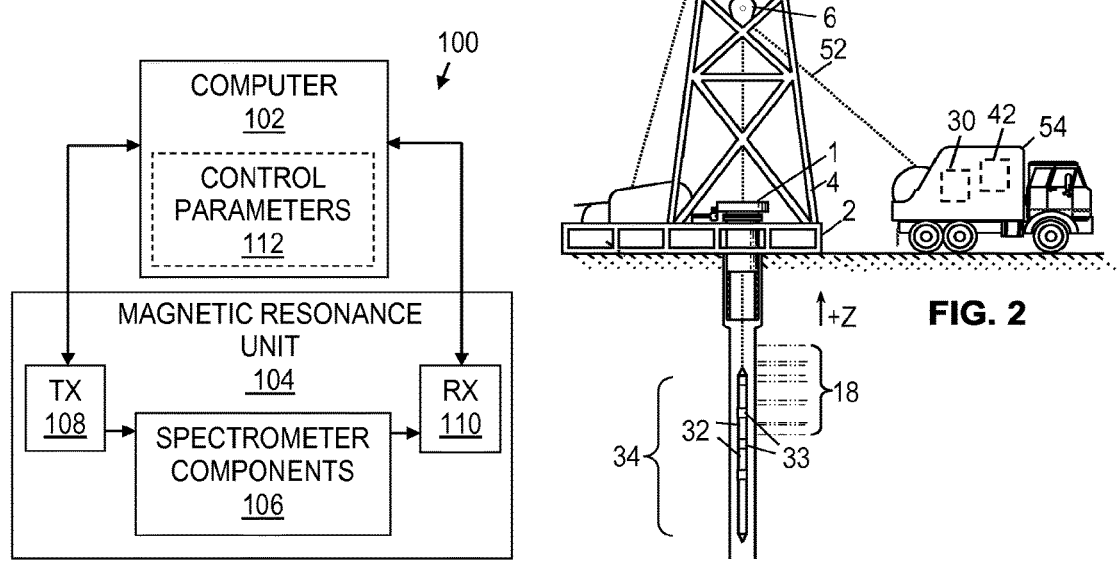
FIG. 3

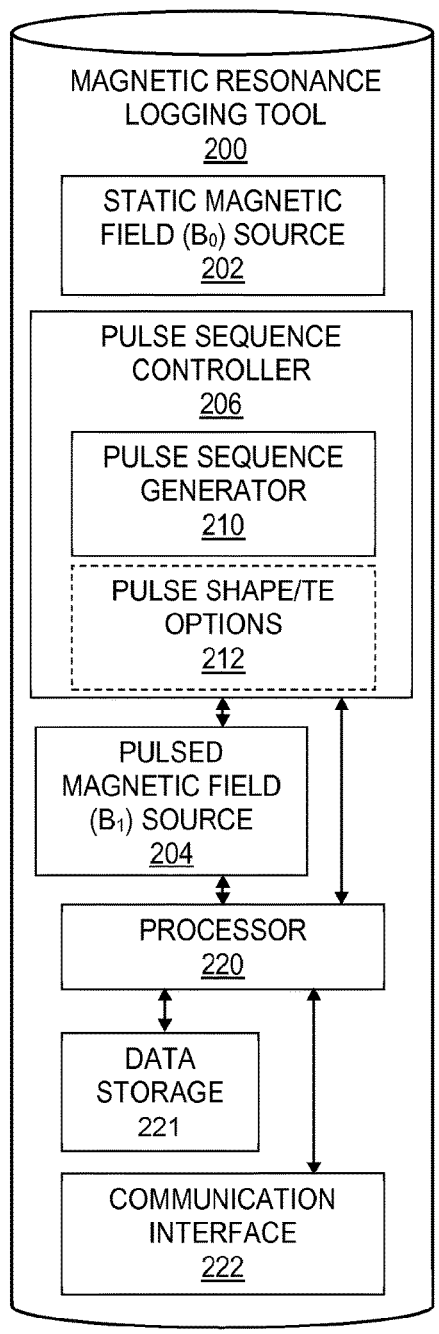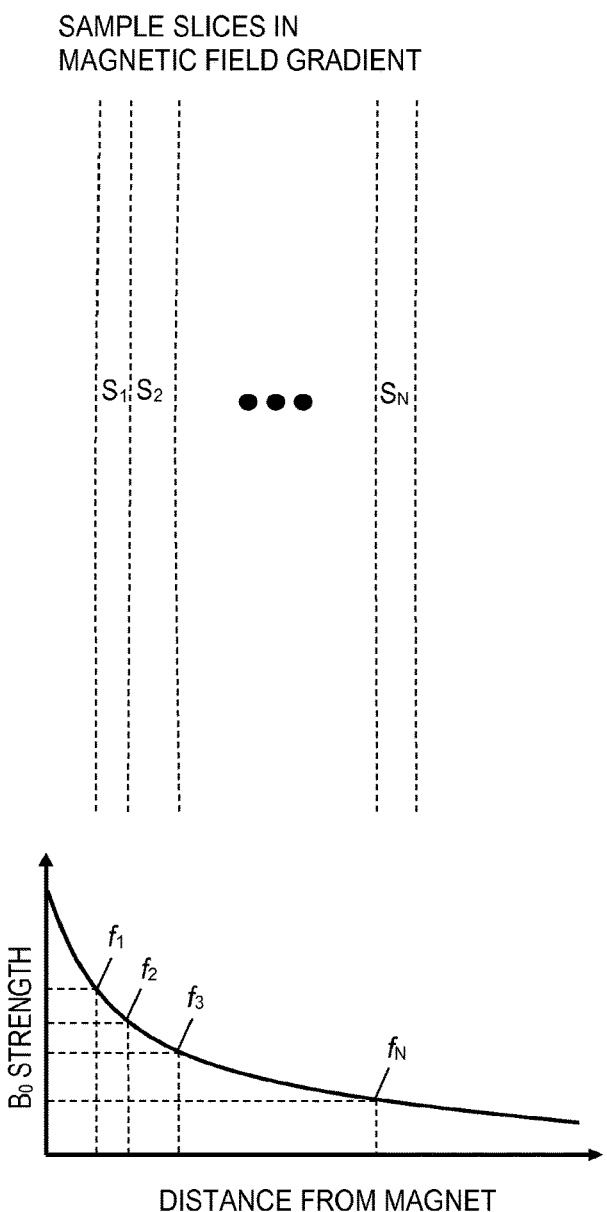
FIG. 4

MAGNETIC RESONANCE SYSTEMS AND METHODS EMPLOYING MULTI-SHAPE PULSE SEQUENCES FOR PARALLEL MEASUREMENTS

BACKGROUND

Understanding the structure and properties of geological formations can improve the efficiency of oil field operations such as drilling, well completion, and production. The collection of information relating to conditions downhole, commonly referred to as "logging," can employ a wide range of downhole instruments including, for example, wireline and logging while drilling ("LWD") nuclear magnetic resonance ("NMR") logging tools.

NMR tools employ a static magnetic field, $B_0$, to give nuclei with non-zero nuclear spin (non-zero magnetic moment and angular momentum) split energy levels. Since lower energy levels are preferred, an ensemble of nuclei will exhibit an anisotropic distribution of energy states, giving the nuclear spins a preferential polarization parallel to the imposed field. This state creates a net magnetic moment and produces a bulk magnetization. The application of this static magnetic field causes the nuclei to converge upon their equilibrium alignment (i.e., to polarize) with a characteristic exponential relaxation time constant. When this convergence occurs after the nuclei have been placed in a cooperative initial state (discussed below), it is known as recovery. The time constant for recovery is called the "spin-lattice" or "longitudinal" relaxation time $T_1$.

During or after the polarization period, the NMR tool applies a perturbing field, usually in the form of a radio frequency electromagnetic pulse whose magnetic component, $B_1$, is perpendicular to the static field $B_0$. This perturbing field moves the orientation of the magnetization into the transverse (perpendicular) plane. Given a static magnetic field strength $B_0$, the frequency of the pulse can be chosen to target specific nuclei (e.g., hydrogen). The polarized nuclei are perturbed simultaneously and, when the perturbation ends, they precess around the static magnetic field gradually re-polarizing to align with the static field once again while losing coherence in the transverse plane ($T_2$ relaxation). Much of their coherence can be restored using a 180° inversion pulse (aka refocusing pulse) at some delay $\tau/2$ after the initial perturbation pulse, leading the precessing nuclei, after another $\tau/2$ delay, to generate a detectable radio frequency "echo" signal having an amplitude that depends on the interecho time $\tau$ and, where a sequence of refocusing pulses is employed, on the total time t since the initial perturbation pulse. With one or more sequences of refocusing pulses, the amplitude dependences of the echoes on interecho time $\tau$ and total time t can be mapped out to enable measurement of the statistical distributions of $T_1$ and/or $T_2$, and based thereon, measurements of porosities, and/or diffusion constants.

The static magnetic field provided by existing downhole NMR logging tools varies as a function of position, yielding the desired static field strength $B_0$ for a given perturbation signal frequency within a relatively well defined measurement region. Unfortunately, existing tools tend to have perturbation pulses with signal sideband energy that extends over a range of frequencies, so that the well-defined measurement region is not the sole source of the echo signal responses. In the past this issue has been ignored or partially addressed by minimizing the signal sideband energy as much as possible within the limits imposed by the design of the tool. While minimizing sideband energy is helpful for achieving desired accuracy for a particular measurement region, existing schemes do not effectively enable comparison of different measurement regions without undesirable delay between the measurements.

BRIEF DESCRIPTION OF THE DRAWINGS

Accordingly, there are disclosed herein various magnetic resonance logging methods and systems employing multi-shape pulse sequence class for parallel measurements. In the figures:

FIG. 1 shows an illustrative logging-while-drilling (LWD) survey environment.

FIG. 2 shows an illustrative wireline logging survey environment.

FIG. 3 is a block diagram of an illustrative magnetic resonance system.

FIG. 4 is a block diagram of an illustrative magnetic resonance logging tool.

Figure 5:
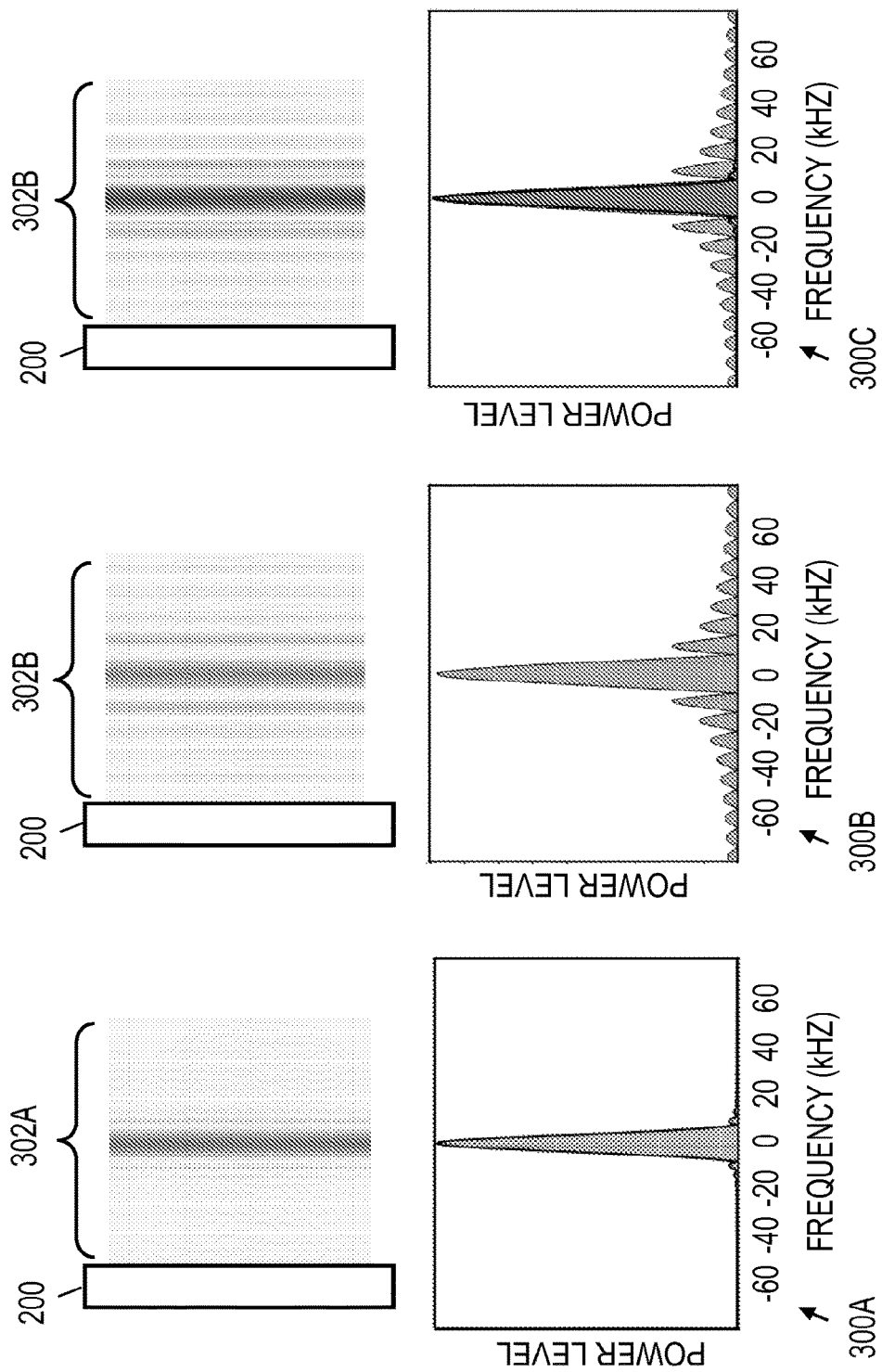
FIGS. 5A-5C show illustrative pulse power spectrums and related measurement region spectrums.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

The following disclosure presents magnetic resonance systems and methods employing a multi-shape pulse sequence class for parallel measurements. As used herein, an "interecho interval" refers to the interval between spin echoes, which interval is controlled by the timing of pulses in the pulse sequence used to generate the echoes. In at least some of the disclosed embodiments, a single pulse sequence affects different measurement regions in presence of a magnetic field gradient and enables efficient collection of echo information that may be stored and processed to determine, for example, a stimulated echo correction, a single-transient diffusion measurement, and/or a porosity calculation correction. In other disclosed embodiments, multiple pulse sequences are used to gather information related to different measurement regions.

The disclosed magnetic resonance systems and methods may be deployed to collect magnetic resonance data in a downhole environment or at earth's surface (e.g., in a laboratory or imaging facility). For example, FIG. 1 shows an illustrative logging-while-drilling (LWD) environment. In FIG. 1, a drilling platform 2 is equipped with a derrick 4 that supports a hoist 6 for raising and lowering a drill string 8. The hoist 6 suspends a top drive 10 suitable for rotating the drill string 8 and lowering the drill string through the well head 12. Connected to the lower end of the drill string 8 is a drill bit 14. As bit 14 rotates, it creates a borehole 16 that passes through various formations 18. A pump 20 circulates drilling fluid through a supply pipe 22 to top drive 10, down through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole 16.

Various materials can be used for drilling fluid, including oil-based fluids and water-based fluids.

In FIG. 1, logging tools 26 are integrated into the bottom-hole assembly 25 near the bit 14. As the bit extends the borehole through the formations, logging tools 26 collect measurements relating to various formation properties as well as the tool orientation and various other drilling conditions. Each of the logging tools 26 may take the form of a drill collar, i.e., a thick-walled tubular that provides weight and rigidity to aid the drilling process. For the present discussion, the logging tools 26 are expected to include a magnetic resonance logging tool. The bottom-hole assembly 25 also may include a telemetry sub 28 to transfer images and/or measurement data to a surface communication interface 30 and to receive commands from the surface. The surface communication interface 30 forwards collected measurements to and/or receives commands from a computer system 42 via a wired or wireless interface 40.

The computer system 42 may perform various operations such as providing commands for logging tools 26, storing logging measurements, processing logging measurements, and displaying related information to an operator. As an example, in at least some embodiments, the computer system 42 includes a processing unit 44 that performs various operations by executing software or instructions obtained from a local or remote non-transitory computer-readable medium 50. The computer system 42 also may include input device(s) 48 (e.g., a keyboard, mouse, touchpad, etc.) and output device(s) 46 (e.g., a monitor, printer, etc.). Such input device(s) 48 and/or output device(s) 46 provide a user interface that enables an operator to interact with the logging tools 26 and/or software executed by the processing unit 44. For example, the computer system 42 may enable an operator to select pulse sequence options, to view collected echoes, to review parameters derived from the echoes (e.g., a stimulated echo correction, a single-transient diffusion measurement, a porosity calculation correction, measurements of T1 and T2 distributions, or other related formation properties), and/or to perform other tasks.

Additionally or alternatively, a magnetic resonance logging tool may include processing, storage, and/or other programming components to select pulse sequences, to store echo information (e.g., amplitude as a function of time), to calculate parameters derived from the stored echo information (e.g., a $T_1$ distribution, a stimulated echo correction, a single-transient diffusion measurement, and/or a porosity calculation correction), and/or to update magnetic resonance logging operations dynamically based on the calculated parameters. Accordingly, a logging tool 26 may be programmed to derive parameters from echoes and to dynamically update logging operations and/or may be responsive to commands from the surface. Such commands from the surface may be generated in response to programmed logging operations performed by computer system 42, parameters derived from collected echoes by computer system 42 or operator, and/or an operator otherwise selecting or entering logging control options via a user interface.

At various times during the drilling process, the drill string 8 may be removed from the borehole 16 as shown in FIG. 2. Once the drill string has been removed, logging operations can be conducted using a wireline logging string 34 suspended by a cable 52 having conductors for transporting power to the logging string (sonde) 34 and telemetry from the logging string 34 to the surface. In some embodiments, the logging string 34 may have pads and/or centralizing members to maintain logging tools 32 near the axis of the borehole as the logging string 34 is pulled uphole. The logging tools 32 may correspond to a variety of logging tools including a magnetic resonance logging tool. A logging facility 54 includes a surface communication interface 30 and a computer system 42 for receiving, storing, and processing measurements gathered by the logging tools 32. The computer system 42 of FIG. 2 may also send commands and/or logging control parameters to the logging tools 32 or perform other operations as described herein.

FIG. 3 shows a block diagram of an illustrative magnetic resonance system 100. The magnetic resonance system 100 may be used for downhole magnetic resonance logging operations (e.g., as in the example survey environments of FIGS. 1 and 2). Alternatively, the magnetic resonance system 100 may be used in a magnetic resonance facility or laboratory at earth's surface. As shown, the magnetic resonance system 100 includes a computer 102 that provides magnetic resonance control parameters 112 for a magnetic resonance unit 104. In at least some embodiments, the magnetic resonance control parameters 112 may be based on firmware/software instructions that are predetermined. Further, the magnetic resonance control parameters 112 may be dynamically determined from analysis of collected measurements. The computer 102 may correspond to a surface computer (e.g., computer system 42 or a lab computer) or a downhole computer (e.g., part of logging tool 26 or 32). In either case, the computer 102 directs the operations of the magnetic resonance unit 104 (e.g., a downhole tool or laboratory equipment), which includes a transmitter (TX) 108, a receiver (RX) 110, and magnetic resonance spectrometer components 106. In at least some embodiments, the computer 102 enables the magnetic resonance unit 104 to collect spin echoes using a multi-shape pulse sequence.

More specifically, the computer 102 is configured to provide commands, programming, and/or data to transmitter 108 of the magnetic resonance unit 104. The transmitter 108 may include a programmable pulse sequence device or storage, a radio frequency (RF) synthesizer, a phase shifter, a pulse gate, an amplifier, and/or other components to control the pulsed magnetic field for magnetic resonance operations including the multi-shape pulse sequence features described herein. Further, in different embodiments, the magnetic resonance control parameters 112 enable adjustment of pulse sequences and receiver window options based on a default configuration, user selection, and/or calibration.

The magnetic resonance unit 104 also includes magnetic resonance spectrometer components 106 used for magnetic resonance operations. Examples of magnetic resonance spectrometer components 106 include one or more magnets, shim coils, probes/antennas, and/or field-frequency lock components. Further, the magnetic resonance spectrometer components 106 may include a duplexer that enables separation between transmission current and reception current. The receiver 110 of magnetic resonance unit 104 is configured to receive and decode magnetic resonance signals. The receiver 110 may include, for example, an analog-to-digital converter (ADC), filters, mixers, splitters, pre-amplifiers, and/or other components to receive magnetic resonance signals and recover measurement data. In accordance with embodiments, receiver 110 is configured to recover spin echo data corresponding to a multi-shape pulse sequence. The recovered measurement data (including at least the amplitudes of the spin echoes) is output from the receiver 110 to computer 102 for storage and/or analysis.

FIG. 4 is a block diagram of an illustrative magnetic resonance logging tool 200, along with an inset graph of the static magnetic field strength ($B_0$) as a function of distance from the tool and with an illustration of multiple sample slices representing the different measurement regions that respond to different signal frequencies. The magnetic resonance logging tool 200 may correspond to, for example, one of logging tools 26, 32 (see FIGS. 1 and 2), magnetic resonance system 100, or magnetic resonance unit 104 (see FIG. 3). As shown, the magnetic resonance logging tool 200 includes a static magnetic field ($B_0$) source 202, such as one or more strong, permanent magnets (e.g., samarium cobalt magnets). The magnetic resonance logging tool 200 also includes a pulsed magnetic field ($B_1$) source 204 to emit pulses of an alternating radio frequency (RF) magnetic field using one or more antennas with suitable electronics. Note that such antennas and electronics can act in a dual role, also functioning to receive and detect spin echo signals. Alternatively, such receiving can be done with separate antennas and electronics.

The magnetic resonance logging tool 200 further includes a pulse sequence controller 206 in communication with the pulsed magnetic field source 204. In some embodiments, the pulse sequence controller 206 includes a pulse sequence generator 210 configured to output, or to direct pulsed magnetic field source 204 to output, a pulse sequence in accordance with pulse shape/TE options 212. The pulse shape/TE options 212 are compliant with magnetic resonance logging tool 200 employing a pulse sequence class with multiple pulse shapes and controllable interecho durations.

In at least some embodiments, the magnetic resonance logging tool 200 also includes data storage 221 for storing instructions and/or echo measurements obtained in response to a multi-shape pulse sequence. Further, the magnetic resonance logging tool 200 may include a processor 220 for processing collected echo measurements and/or deriving a parameter (e.g., a stimulated echo correction, a single-transient diffusion measurement, and/or a porosity calculation correction) based on the collected echo measurements. The processor 220 also may update operations of the pulse sequence controller 206 as needed. Such updates may be based on the derived parameters, calibration operations, or instructions received via communication interface 222. The communication interface 222 may also enable transmission of collected echo measurements, processed echo measurements, and/or derived parameters to earth's surface.

In operation, the magnetic resonance logging tool 200 can affect spins in different measurement regions in presence of a magnetic field gradient. The magnetic field gradient, for example, may be due to $B_0$ changing as a function of distance from the static magnetic field source 202 as shown, or due to spatial distribution of the pulsed magnetic field. Regardless of the exact cause, it is typical for different measurement regions to respond to different frequencies of the pulsed magnetic field source 204 (e.g., frequencies $f_1$-$f_N$) couple to different measurement regions (e.g., slices $S_1$-$S_N$).

FIGS. 5A-5C show illustrative pulse power spectrums (at baseband) and related measurement region distributions relative to magnetic resonance logging tool 200 (an ex-situ magnetic resonance configuration). The pulse sequence class described herein may also be used for in-situ magnetic resonance configurations. In FIG. 5A, a Hahn pulse power spectrum 300A is represented, and includes a main lobe and very small side lobes. As a result, the measurement region 302A that responds to the Hahn pulse is focused well on a particular measurement region due to the narrow bandwidth of the Hahn pulse. In FIG. 5B, a square pulse power spectrum 300B is represented, and includes a main lobe and various notable side lobes. The measurement region 302B that responds to the square pulse has a number of extraneous fringes. That is, the measurement region is extended relative to that of the Hahn pulse due to the larger bandwidth of the square pulse. If the two measurement regions and spectra were to be overlaid, as shown in FIG. 5C, one would observe a notable overlap of the primary measurement regions resulting from the main lobes of the Hahn and square pulse power spectra, and a secondary measurement region that is interrogated by the square pulse but not the Hahn pulse.

For a given magnetic field gradient, the spectrum of the pulses used determine the excitation volume (i.e., the measurement region). Thus, different pulse shapes select different measurement regions of a sample, and yield different tip angle distributions. However, the inhomogeneous nature of the magnetic field gradient creates an opportunity to use multiple pulse power spectra that affect different measurement regions in the same pulse sequence.

Figure 6:
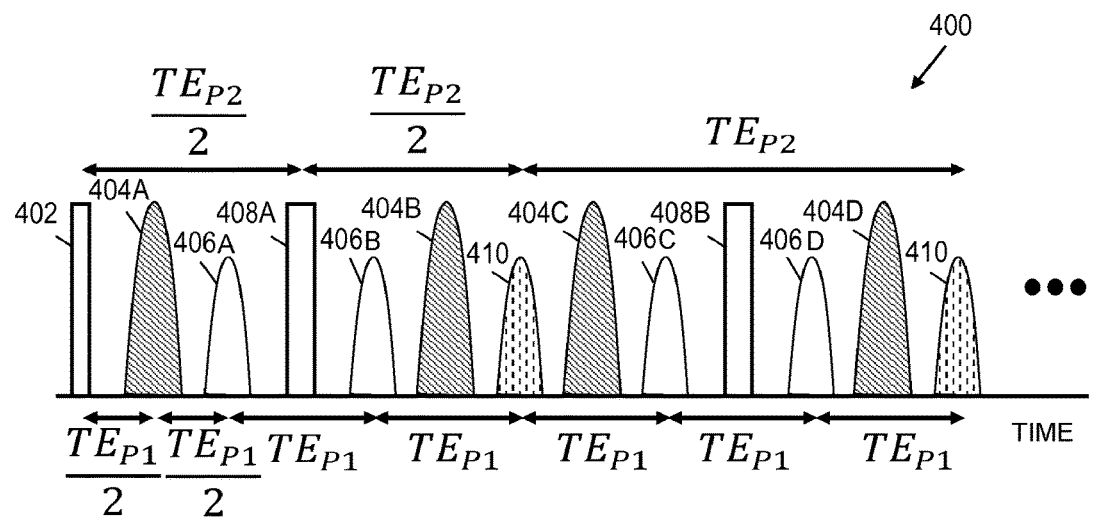
FIG. 6 shows an illustrative pulse sequence.

FIG. 6 shows an illustrative pulse sequence 400. As shown, the pulse sequence 400 begins with an excitation pulse 402 to tip the nuclear spins perpendicular to the static field (i.e., a 90° shift). After the excitation pulse 402, a repeating pattern of refocusing pulses including narrowband pulses 404 and wideband pulses 403 are applied to generate spin echoes, where the narrowband pulses 404 and wideband pulses 408 have overlapping main lobes as described herein. The illustrated pattern provides the pulse sequence 400 with two measurement regions that are driven with different characteristic IF values. The first narrowband pulse 404A is a refocusing pulse, which occurs at time $t=TE_{P1}/2$, causing an echo 406A corresponding to the main lobe spins at time $t=TE_{P1}$. The first wideband pulse 408A is another refocusing pulse at $t=3TE_{P1}/2$, which inverts the spins in both the main lobe measurement region and the side lobe measurement region. Since the main lobe spins were last coherent at $t=TE_{P1}$, the corresponding echo 406B will occur at time $t=2TE_{P1}$ as they would if wideband pulse 408A were a narrowband pulse. Further, the side lobe spins were last coherent at $t=0$, and so the side lobe measurement region produces a corresponding echo 410 at time $t=3TE_{P1}=TE_{P2}$. Meanwhile, the second narrowband pulse 404B at time $t=3TE_{P1}/2$ refocuses the main lobe spins again. Accordingly, the spin echo signal 410 at time $t=3TE_{P1}$ is a combination of both of the signal produced by main lobe spins and the signal produced by the side lobe spins. The same pattern is repeated with narrowband pulse 404C, wideband pulse 408B, and narrowband pulse 404D. Although only two repetitions of the pattern are shown for pulse sequence 400, it should be understood that additional repetitions of the pattern could be used to monitor the spin echo amplitudes over an extended period of time. Further, it should be understood that other patterns are possible as described herein.

In at least some embodiments, the pulse sequence generator 210 generates or selects a pulse sequence with a repeated pulse pattern P1-P2-P1, where P1 and P2 correspond to different pulse shapes and where $TE_{P2}=3TE_{P1}$ (as in FIG. 6). As another example, the pulse sequence generator 210 may generate or select a repeated pulse pattern P1-P1-P2-P1-P1, where $P_1$ and $P_2$ correspond to different pulse shapes and where $TE_{P2}=5TE_{P1}$. As yet another example, the pulse sequence generator 210 may generate or select a pulse sequence with a repeated pulse pattern P1-P2-P1-P1-P3-P1-P1-P2-P1, where P1, P2, and P3 correspond to different pulse shapes, and where $TE_{P2}=3TE_{P1}$ and $TE_{P3}=9TE_{P1}$. In the above example patterns, P1 is narrower than P2 and the power spectrum of P1 is substantially included in the power spectrum of P2. Further, P2 is narrower than P3 and the power spectrum of P2 is substantially included in the power spectrum of P3. As an example, P1 may correspond to a Hahn pulse, P2 may correspond to a square pulse or a Hahn pulse variant with 3 lobes, and P3 may correspond to a square pulse or a Hahn pulse variant with 5 lobes. The above Hahn pulse variants have multiple lobes that are tightly-packed and non-overlapping. Generally, Hahn pulse variants that may be used include a main Hahn pulse with side Hahn pulses that are offset from the main Hahn pulse and from each other.

Regardless of the pulse shapes used, it should be understood that the main power spectrum lobes (hereafter referred to simply as "main lobes" herein) of the different pulses preferably overlap. Further, the side power spectrum lobes (hereafter referred to simply as "side lobes" herein) of the different pulses may or may not overlap. For example, in the above examples, the main lobes of P1, P2, and P3 substantially overlap, and any side lobes of P1 do not substantially overlap with sides lobes of P2 or P3. Meanwhile, the side lobes of P2 substantially overlap with some of the side lobes of P3.

One way to describe the pulses used in the disclosed pulse sequence class is that the power spectrum of the pulses used partially overlap. For example, assume distinct (little or no overlap) frequency bands A-C, where A refers a frequency band that includes a main lobe, B refers a frequency band that includes a first set of side lobes, and C refers to a frequency band that includes a second set of side lobes. With this notation, the repeated patterns used for a pulse sequence may be given as $P_A\text{-}P_{AB}\text{-}P_A$, $P_A\text{-}P_A\text{-}P_{AB}\text{-}P_A\text{-}P_A$, $P_A\text{-}P_{AB}\text{-}P_A\text{-}P_A\text{-}P_{ABC}\text{-}P_A\text{-}P_A\text{-}P_{AB}\text{-}P_A$. Other repeated patterns are possible. For example, a repeated pattern may employ pulses: $P_A$, $P_{AB}$, $P_{AC}$, and $P_{ABC}$. Further, if D refers to another distinct frequency band that includes a third set of side lobes, a repeated pattern may employ pulses: $P_A$, $P_{AB}$, $P_{AC}$, $P_{AD}$, $P_{ABC}$, $P_{ABD}$, $P_{ACD}$, and $P_{ABCD}$. When using multiple pulses at relatively-prime multiples, the "product pulses" have to cover all of the frequency bands excited by the two pulses. For example, if $P_{AB}$ occurs at time 3TE and $P_{AC}$ occurs at time 5TE, then $P_{ABC}$ will occur at time 15TE.

There are many potential uses for the class of pulse sequences described herein. For example, to the extent that the stimulated echo effect depends on pulse angle distribution and TE, varying either or both of these things within a single transient could allow the stimulated echo effect to be dynamically corrected for using the difference in effect between the relevant echoes. Further, this general class of pulse sequence may also allow single-transient measurements of diffusion, as the effect of diffusion is primarily measured by the response of $T_2$ to a change in TE, which could significantly increase the vertical resolution of non-stationary diffusion measurements. Another potential use for this general class of pulse sequence would to obtain more accurate porosity measurements by better correcting for the effect of the pulse shape on the porosity calculation with a form of internal check.

Figure 7:
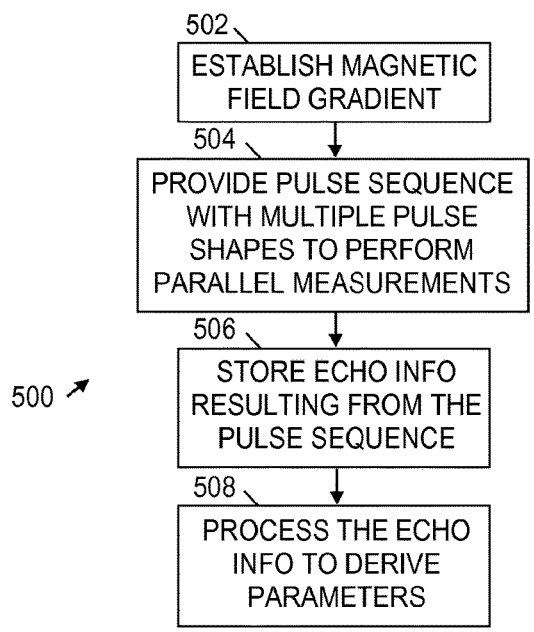
FIG. 7 shows a flowchart of an illustrative magnetic resonance method.

FIG. 7 is a flowchart for an illustrative magnetic resonance method 500. The method may be performed, for example, by a logging tool 26, 32, 200, or magnetic resonance system 100. At block 502, a magnetic field gradient is established. At block 504, a pulse sequence with multiple pulse shapes and multiple characteristic TEs is provided as described herein. At block 506, echo information 506 resulting from the pulse sequence is stored. At block 508, the stored echo information is processed to derive parameters. Example parameters that may be derived at block 508 include a $T_1$ distribution, a stimulated echo correction, a single-transient diffusion measurement, and/or a porosity calculation correction.

Embodiments disclosed herein include:

A: A magnetic resonance (MR) method that comprises providing a pulse sequence that affects different measurement regions in presence of a magnetic field gradient, the pulse sequence having multiple pulse shapes and multiple characteristic interecho intervals (TEs); and storing echo information resulting from the pulse sequence.

B: A magnetic resonance (MR) system that comprises a static magnetic field source, a pulsed magnetic field source, a controller, and a data storage unit. The controller provides a pulse sequence that affects different measurement regions in presence of a magnetic field gradient, the pulse sequence having multiple pulse shapes and multiple characteristic interecho intervals (TEs). The data storage unit stores echo information resulting from the pulse sequence.

Each of the embodiments, A and B, may have one or more of the following additional elements in any combination. Element 1: further comprising selecting the pulse sequence from a plurality of pulse sequence options, each option having a different combination of multiple pulse shapes and multiple characteristic interecho intervals (TEs). Element 2: the pulse sequence comprises a repeated pulse pattern P1-P2-P1, where P1 and P2 correspond to different pulse shapes and where $TE_{P2}=3TE_{P1}$. Element 3: the pulse sequence comprises a repeated pulse pattern P1-P1-P2-P1-P1, where P1 and P2 correspond to different pulse shapes and where $TE_{P2}=5TE_{P1}$. Element 4: the pulse sequence comprises a repeated pulse pattern P1-P2-P1-P1-P3-P1-P1-P2-P1, where P1, P2, and P3 correspond to different pulse shapes, and where $TE_{P2}=3TE_{P1}$ and $TE_{P3}=9TE_{P1}$. Element 5: the multiple pulse shapes comprise a first pulse and a second pulse, wherein a power spectrum of the first pulse is narrower than and at least substantially included in the power spectrum of the second pulse. Element 6: the first pulse corresponds to a Hahn pulse. Element 7: the second pulse corresponds to a square pulse. Element 8: the second pulse corresponds to a Hahn pulse variant with a main Hahn pulse between at least two side Hahn pulses offset from the main Hahn pulse. Element 9: the first pulse and the second pulse have main power spectrum lobes that substantially overlap. Element 10: further comprising performing a stimulated echo correction based on the stored echo information. Element 11: further comprising performing a single-transient diffusion measurement based on the stored echo information. Element 12: further comprising comparing an effect of each of the multiple pulse shapes on a porosity calculation using the stored echo information, and correcting the porosity calculation based on the comparison.

Element 13: the controller generates the pulse sequence using a repeated pulse pattern having a first pulse and a second pulse, where a power spectrum of the first pulse is narrower than the power spectrum of the second pulse, and wherein the power spectrum of the first pulse is substantially included in the power spectrum of second pulse. Element 14: wherein the controller generates the pulse sequence using a repeated pulse pattern having a first pulse, a second pulse, and a third pulse, wherein a power spectrum of the first pulse is narrower than and at least substantially included in the power spectrum of the second pulse, and wherein a power spectrum of the second pulse is narrower than and at least substantially included in the power spectrum of the third pulse. Element 15: the controller generates the pulse sequence using a Hahn pulse and a square pulse with main power spectrum lobes that substantially overlap. Element 16: the controller selects the pulse sequence from a plurality of pulse sequence options, each option having a different combination of multiple pulse shapes and multiple characteristic interecho intervals (TEs). Element 17: further comprising a processing unit that performs at least one of a stimulated echo correction and a single-transient diffusion measurement based on the stored echo information. Element 18: further comprising a processing unit that compares an effect of each of the multiple pulse shapes on a porosity calculation using the stored echo information, and corrects the porosity calculation based on the comparison.

Numerous other variations and modifications will become apparent to those skilled in the art once the above disclosure is fully appreciated. It is intended that the following claims be interpreted to embrace all such variations and modifications where applicable.

What is claimed is:

1. A magnetic resonance (MR) method, comprising:
providing a pulse sequence that affects different measurement regions in the presence of a magnetic field gradient, the pulse sequence having multiple pulse shapes and multiple characteristic interecho intervals (TEs), wherein the multiple pulse shapes comprise a first pulse and a second pulse, and wherein a power spectrum of the first pulse is narrower than and at least substantially included in the power spectrum of the second pulse; and
storing echo information resulting from the pulse sequence.

2. The method of claim 1, further comprising selecting the pulse sequence from a plurality of pulse sequence options, each option having a different combination of multiple pulse shapes and multiple characteristic interecho intervals (TEs).

3. The method of claim 1, wherein the pulse sequence comprises a repeated pulse pattern P1-P2-P1, where P1 and P2 correspond to different pulse shapes, wherein a first time period $TE_{P2}$ including the repeated pulse pattern has a duration in time equal to a second time period $3TE_{P1}$, and wherein $TE_{P1}$ is an interecho interval between subsequent echoes.

4. The method of claim 1, wherein the pulse sequence comprises a repeated pulse pattern P1-P1-P2-P1-P1, where P1 and P2 correspond to different pulse shapes, wherein a first time period $TE_{P2}$ including the repeated pulse pattern has a duration in time equal to a second time period $5TE_{P1}$, and wherein $TE_{P1}$ is an interecho interval between subsequent echoes.

5. The method of claim 1, wherein the pulse sequence comprises a repeated pulse pattern P1-P2-P1-P1-P3-P1-P1-P2-P1, where P1, P2, and P3 correspond to different pulse shapes, wherein a first time period $TE_{P2}$ including the repeated pulse pattern has a duration in time equal to a second time period $3TE_{P1}$ and a third time period $TE_{P3}$ including the repeated pulse pattern has a duration in time equal to a fourth time period $9TE_{P1}$, and wherein $TE_{P1}$ is an interecho interval between subsequent echoes.

6. The method of claim 1, wherein the first pulse corresponds to a Hahn pulse.

7. The method of claim 1, wherein the second pulse corresponds to a square pulse.

8. The method of claim 1, wherein the second pulse corresponds to a Hahn pulse variant with a main Hahn pulse between at least two side Hahn pulses offset from the main Hahn pulse.

9. The method of claim 1, wherein the first pulse and the second pulse have main power spectrum lobes that substantially overlap.

10. The method of claim 1, further comprising performing a stimulated echo correction based on the stored echo information.

11. The method of claim 1, further comprising comparing an effect of each of the multiple pulse shapes on a porosity calculation using the stored echo information, and correcting the porosity calculation based on the comparison.

12. A magnetic resonance (MR) system, comprising:
a static magnetic field source;
a pulsed magnetic field source; and
a controller to provide a pulse sequence that affects different measurement regions in presence of a magnetic field gradient, the pulse sequence having multiple pulse shapes and multiple characteristic interecho intervals (TEs)), wherein the multiple pulse shapes comprise a first pulse and a second pulse, and wherein a power spectrum of the first pulse is narrower than and at least substantially included in the power spectrum of the second pulse; and
a data storage unit for storing echo information resulting from the pulse sequence.

13. The system of claim 12, wherein the controller generates the pulse sequence using a repeated pulse pattern including the first pulse and the second pulse.

14. The system of claim 12, wherein the controller generates the pulse sequence using a repeated pulse pattern including the first pulse, the second pulse, and a third pulse, wherein a power spectrum of the second pulse is narrower than and at least substantially included in the power spectrum of the third pulse.

15. The system of claim 12, wherein the controller generates the pulse sequence using a Hahn pulse and a square pulse with main power spectrum lobes that substantially overlap.

16. The system of claim 12, wherein the controller selects the pulse sequence from a plurality of pulse sequence options, each option having a different combination of multiple pulse shapes and multiple characteristic interecho intervals (TEs).

17. The system of claim 12, further comprising a processing unit that compares an effect of each of the multiple pulse shapes on a porosity calculation using the stored echo information, and corrects the porosity calculation based on the comparison.

* * * * *